(12) United States Patent
Tas et al.

(10) Patent No.: US 7,893,078 B2
(45) Date of Patent: Feb. 22, 2011

(54) USE OF CYCLOPAMINE IN THE TREATMENT OF BASAL CELL CARCINOMA AND OTHER TUMORS

(75) Inventors: Sinan Tas, Yasemin Sokak 6, Sahilevleri, Narlidere, Izmir (TR) 35320; Oktay Avci, Izmir (TR)

(73) Assignee: Sinan Tas, Bor (TR)

( * ) Notice: Subject to any disclaimer, the term of this patent is extended or adjusted under 35 U.S.C. 154(b) by 0 days.

(21) Appl. No.: 10/682,584

(22) Filed: Oct. 9, 2003

(65) Prior Publication Data

US 2004/0072914 A1 Apr. 15, 2004
US 2010/0048725 A2 Feb. 25, 2010

Related U.S. Application Data

(63) Continuation-in-part of application No. PCT/TR02/00017, filed on Apr. 19, 2002, and a continuation-in-part of application No. PCT/TR01/00027, filed on Jul. 2, 2001.

(51) Int. Cl.
*A61K 31/438* (2006.01)
(52) U.S. Cl. .................................. 514/278
(58) Field of Classification Search ............... 514/47, 514/469, 310, 278
See application file for complete search history.

(56) References Cited

U.S. PATENT DOCUMENTS

| | | | | |
|---|---|---|---|---|
| 5,891,465 A * | 4/1999 | Keller et al. | ............ | 424/450 |
| 6,238,876 B1 | 5/2001 | Altaba | | |
| 6,291,516 B1 * | 9/2001 | Dudek et al. | ............ | 514/455 |
| 6,432,970 B2 * | 8/2002 | Beachy et al. | ............ | 514/278 |
| 6,686,388 B2 * | 2/2004 | Dudek et al. | ............ | 514/455 |
| 6,867,216 B1 * | 3/2005 | Beachy et al. | ............ | 514/278 |
| 7,291,626 B1 * | 11/2007 | Beachy et al. | ............ | 514/278 |
| 2002/0165221 A1 | 11/2002 | Baxter et al. | | |
| 2003/0022819 A1 | 1/2003 | Ling et al. | | |
| 2003/0139457 A1 | 7/2003 | Baxter et al. | | |
| 2004/0023949 A1 | 2/2004 | Baxter et al. | | |
| 2004/0060568 A1 | 4/2004 | Dudeck et al. | | |
| 2004/0072913 A1 * | 4/2004 | Tas et al. | ............ | 514/649 |
| 2004/0072914 A1 | 4/2004 | Tas et al. | ............ | 514/649 |
| 2004/0110663 A1 | 6/2004 | Dudeck et al. | ............ | 514/2 |
| 2004/0127474 A1 | 7/2004 | Dudeck et al. | | |
| 2005/0014796 A1 | 1/2005 | Baxter et al. | | |
| 2005/0054568 A1 | 3/2005 | Ling et al. | | |
| 2005/0080138 A1 | 4/2005 | Guicherit et al. | | |
| 2005/0112707 A1 | 5/2005 | Altaba et al. | ............ | 435/7.23 |
| 2005/0130922 A1 | 6/2005 | Altaba et al. | | |

FOREIGN PATENT DOCUMENTS

| | | |
|---|---|---|
| KR | 2005037103 | 4/2005 |
| WO | WO 98/35020 | 8/1998 |
| WO | 99/52534 A | 10/1999 |
| WO | 00/41545 A | 7/2000 |
| WO | 00/74706 A | 12/2000 |
| WO | WO 00/74706 | 12/2000 |
| WO | 01/27135 A | 4/2001 |
| WO | 01/40438 A | 6/2001 |
| WO | WO 01/98344 | 12/2001 |
| WO | WO 02/07702 | 1/2002 |
| WO | WO 02/30462 | 4/2002 |
| WO | WO 02/080952 | 10/2002 |

OTHER PUBLICATIONS

Goodman &Gilman'S, The Pharmacological Basis of Therapeutics, Ninth Edition, (1996), Calabresi et al., Section X, Chemotherapy of Neoplastic Diseases, pp. 1225-1229.*

Chen et al., "Analysis of the zebrafish smoothened mutant reveals conserved and divergent functions of hedgehog activity." Development 128, 2385-2396 (2001).

U.S. Appl. No. 60/240,564, filed Oct. 13, 2000.

Hutchin, M.E., et al, "Sustained Hedgehog signaling is required for basal cell carcinoma proliferation and survival: conditional skin tumorigenesis recapitulates the hair growth cycle," *Genes & Development* 19:214-223 (2005).

Sanchez P et, al , "In vivo inhibition of endogenous brain tumors through systemic interference of Hedgehog signaling in mice," *Mechanisms of Development* 2005;122:223-230.

(Continued)

*Primary Examiner*—James D Anderson
(74) *Attorney, Agent, or Firm*—Vidas, Arrett & Steinkraus

(57) ABSTRACT

This invention concerns the use of cyclopamine in vivo on basal cell carcinomas (BCC's) to achieve therapeutic effect by causing differentiation of the tumor cells and, at the same time, apoptotic death and removal of these tumor cells while preserving the normal tissue cells, including the undifferentiated cells of the normal epidermal basal layer and hair follicles. Causation of apoptosis by cyclopamine is by a non-genotoxic mechanism and thus unlike the radiation therapy and most of the currently used cancer chemotherapeutics which act by causing DNA-damage. These novel effects, previously unachieved by a cancer chemotherapeutic, make the use of cyclopamine highly desirable in cancer therapy, in the treatment of BCC's and other tumors that use the hedgehog/smoothened signal transduction pathway for proliferation and prevention of apoptosis.

23 Claims, 2 Drawing Sheets
(2 of 2 Drawing Sheet(s) Filed in Color)

OTHER PUBLICATIONS

Vila, G., et al, "Expression and Function of Sonic Hedgehog Pathway Components in Pituitary Adenomas: Evidence for a Direct Role in Hormone Secretion," *Journal of Clinical Endocrinology & Metabolism*, 90(12)6687-6694 (2005).

Fujita E et al, "Involvement of *Sonic hedgehog* in the Cell Growth of LK-2 Cells, Human Lung Squamous Carcinoma Cells," *Biochem Biophys Res Commun* 1997;238:658-664.

Jimenez et al. "Ber-EP4 Immunoreactivity in Normal Skin and Cutaneous Neoplasms." Modern Pathology, vol. 8, No. 8, pp. 854-858. 1995.

Baker et al. "Lesions of Potato Sprout and Extracted Potato Sprout Alkaloid Toxicity in Syrian Hamsters" Clinical Toxicology. 25(3). pp. 199-208. 1987.

Takechi et al. "Structure-Activity Relationships of Synthetic Saponins" Phytochemistry, vol. 41, No. 1, pp. 121-123, 1996.

Zhang et al. "Effect of six steroidal saponins isolated from anemarrhenae rhizoma on platelet aggregation and hemolysis in human blood" Clinica Chimica Acta 289. pp. 79-88. 1999.

Ericson et al. "Two Critical Periods of Sonic Hedgehog Signaling Required for the Specification of Motor Neuron Identity" Cell, vol. 87, 661-673, Nov. 15, 1996.

Barnes et al. "Patched1 interacts with cyclin B1 to regulate cell cycle progression" The EMBO Journal vol. 20 No. 9 pp. 2214-2223, 2001.

Diehl et al. "Glycogen synthase kinase-3b regulates cyclin D1 proteolysis and subcellular localization" Genes & Development. 12:3499-3511. 1998.

Nasevicius A et al. "Effective targeted gene 'knockdown' in zebrafish" Nature Genetics. 2000; 26:216-220.

De Boer et al. "Expression of Ep-CAM in Normal, Regenerating, Metaplastic, and Neoplastic Liver" Journal of Pathology. 188:201-206. 1999.

Kubuschok et al. "Disseminated Tumor Cells in Lymph Nodes as a Determinant for Survival in Surgically Resected Non-Small-Cell Lung Cancer" Journal of Clinical Oncology. vol. 17. No. 1. pp. 19-24. 1999.

Xu et al. "Genomewide Expression Profiling in the Zebrafish Embryo Identifies Target Genes Regulated by Hedgehog Signaling During Vertebrate Development" Genetics. 174:735-752. Oct. 2006.

Stamataki et al. "A gradient of Gli activity mediates graded Sonic Hedgehog signaling in the neural tube" Genes & Development. 19:626-641. 2005.

Moztny et al. "The *Drosophila cubitus* interruptus protein and its role in the wingless and hedgehog signal transduction pathways" Mechanisms of Development. pp. 137-150. 1995.

Jorns et al. "Comparative toxicity of alloxan, N-alkylalloxans and ninhydrin to isolated pancreatic islets in vitro" Journal of Endocrinology. 155:283-293. 1997.

Goodrich et al. "Hedgehog and Patched in Neural Development and Disease" Neuron. vol. 21. pp. 1243-1257. Dec. 1998.

Coventry et al. "Cyclopamine-Induced Holoprosencephaly and Associated Craniofacial Malformations in the Golden Hamster: Anatomic and Molecular Events" Pediatric and Developmental Pathology. 1:29-41. 1998.

DasGupta et al. "A case study of the reproducibility of transcriptional reporter cell-based RNAi screens in *Drosophila*" Genome Biology. vol. 8, Issue 9, Article R203. 2007.

Wang et al. "Nuclear import of Cubitus interruptus is regulated by Hedgehog via a mechanism distinct from Ci stabilization and Ci activation" Development. 127:3131-3139. 2000.

Methot et al. "An absolute requirement for Cubitus interruptus in Hedgehog signaling" Development. 128:733-742. 2001.

Bai et al. "All Mouse Ventral Spinal Cord Patterning by Hedgehog Is Gli Dependent and Involves an Activator Function of Gli3" Developmental Cell. vol. 6, 103-115. Jan. 2004.

Chiang C et al. "Cyclopia and defective axial patterning in mice lacking Sonic hedgehog gene function" Nature. 1996; 383:407-413.

Krauss S et al. "A Functionally Conserved Homolog of the *Drosophila* Segment Polarity Gene hh is Expressed in Tissues with Polarizing Activity in Zebra Embryos" Cell. 1993; 75:1431-1444.

Bucana et al. "Different Patterns of Macrophage Infiltration into Allogeneic-murine and Xenogeneic-human Neoplasms Growing in Nude Mice" American Journal of Pathology. vol. 141, No. 5. Nov. 1992.

Jaye et al. "Expression of acidic fibroblast growth factor cDNA confers growth advantage and tumorigenesis to Swiss 3T3 cells" The EMBO Journal. vol. 7 No. 4. pp. 963-969. 1988.

Ananthaswamy et al. "Detection and Identification of Activated Oncogenes in Human Skin Cancers Occurring on Sun-exposed Body Sites" Cancer Research. 48:3341-3346. Jun. 15, 1988.

Lewis et al. "Tumor Induction by the c-Myc Target Genes rcl and Lactate Dehydrogenase A" Cancer Research. 60:6178-6183. Nov. 1, 2000.

Wilson et al. "Malignant Transformation of Human Fibroblasts by a Transfected N-ras Oncogene" Cancer Research. 50:5587-5593. Sep. 1, 1990.

Taghian et al. "Quantitative Comparison between the Transplantability of Human and Murine Tumors into the Subcutaneous Tissue of NCr/Sed-nu/nu Nude and Severe Combined Immunodeficient Mice" Cancer Research. 53:5012-5017. Oct. 1993.

De Jong et al. "Number of apoptotic cells as a prognostic marker in invasive breast cancer" British Journal of Cancer. 82(2), 368-373. 2000.

Zietman et al. "Quantitative Studies on the Transplantability of Murine and Human Tumors into the Brain and Subcutaneous Tissues of NCr/Sed Nude Mice" Cancer Research. 48:6510-6516. Nov. 15, 1988.

Auerbach et al. "Regional Differences in the Incidence and Growth of Mouse Tumors following Intradermal or Subcutaneous Inoculation" Cancer Research. 38:1739-1744. Jun. 1978.

Kampschmidt et al. "Acid Hydrolase Activity during the Growth, Necrosis, and Regression of the Jensen Sarcoma" Cancer Research. 28:1938-1943. Oct. 1968.

Hannun Ya. "Apoptosis and the Dilemma of Cancer Chemotherapy" Blood. 1997; 89:1845-1853.

Willingham MC. "Cytochemical Methods for the Detection of Apoptosis" The Journal of Histochemistry and Cytochemistry. 1999; 47:1101-1109.

Review of Medical Pharmacology, 7th edition Meyers FH et al, Lange Medical Publications, Los Altos, CA, U.S.A., 1980.

Birkeland KI, Diabetic Medicine 1998;15:S13-S19.

Cannavo S et al, Journal of Endocrinological Investigation 1999;22:354-359.

Soignet SL et al; New England Journal of Medicine; 1998;339:1341-1348.

Romer JT et al., "Suppression of the Shh pathway using a small molecule inhibitor eliminates medulloblastoma in Ptc1+/-p53-/- mice" Cancer Cell : Sep. 2004 vol. 6 pp. 229-240.

Symmans WF et al., "Paclitaxel-induced Apoptosis and Mitotic Arrest Assessed by Serial Fine-Needle Aspiration: Implications for Early Prediction of Breast Cancer Response to Neoadjuvant Treatment1" Clinical Cancer Research, vol. 6, 4610-4617, Dec. 2000.

van de Schepop, Ham et al., "Counting of apoptotic cells: a methodological study in invasive breast cancer" J Clin Pathol: Mol Pathol 1996;49:M214-M217.

Guenther, ST et al.; "Cutaneous squamous cell carcinomas consistently show histologic evidence of in situ changes: A clinicopathologic correlation," J Am Acad Dermatol, vol. 41, No. 3, Part 1; Sep. 1999; pp. 443-448.

Jackson, R. et al.; "Elderly and sun-affected skin" Can Fam Physician 2001;47:1236-1243.

Katsuura, M. et al.; "The NH2-terminal region of the active domain of sonic hedgehog is necessary for its signal transduction" FEBS Letters 447 (1999) 325-328.

Yashiro, K. et al.; "Actinic keratoses arising only on sun-exposed vitiligo skin" Clinical and Experimental Dermatology, 24, 199-201 (1999).

Yoshimura, M.D., K. et al.; "Usefulness of a Narrow-Band Reflectance Spectrophotometer in Evaluating Effects of Depigmenting Treatment" Aesth. Plast. Surg. 25:129-133, 2001.

Levine, Edward M. et al., Sonic Hedgehog Promotes Rod Photoreceptor Differentiation in Mammalian Retinal Cells In Vitro, *The Journal of Neuroscience*, Aug. 15, 1997, 17(16):6277-6288.

Kim, Seung K. et al., "Pancreas development is promoted by cyclopamine, a Hedgehog signaling inhibitor," *Proc. Natl. Acad. Sci. USA*, vol. 95, pp. 13036-13041, Oct. 1998, Developmental Biology.

Incardona, John P. et al., "The teratogenic Veratrum alkaloid cyclopamine inhibits Sonic hedgehog signal transduction," *Development 125*, pp. 3553-3562 (1998), Printed in Great Britain © The Company of Biologists Limited 1998.

Cooper, Michael K., "Teratogen-Mediated Inhibition of Target Tissue Responses to Shh Signaling," www.sciencemag.org, *Science*, vol. 280, pp. 1603-1607 (Jun. 5, 1998).

Stenkamp, Deborah L., "Function for *Hedgehog* Genes in Zebrafish Retinal Development," Developmental Biology, vol. 220, pp. 238-252 (2000).

Treier, Mathias et al., "Hedgehog signaling is required for pituitary gland development," *Development 128*, pp. 377-386 (2001), Printed in Great Britain © The Company of Biologists Limited 2001.

Kahane, Nitza et al., "The third wave of myotome colonization by mitotically competent progenitors: regulating the balance between differentiation and proliferation during muscle development," *Development 128*, pp. 2187-2198 (2001), Printed in Great Britain © The Company of Biologists Limited 2001.

Fan, Hongran et al., "Sonic Hedgehog Opposes Epithelial Cell Cycle Arrest," *The Journal of Cell Biology*, vol. 147, No. 1, Oct. 4, 1999, pp. 71-76.

Sukegawa, Akiko et al., "The concentric structure of the developing gut is regulated by Sonic hedgehog derived from endodermal epithelium," *Development 127*, pp. 1971-1890 (2000), Printed in Great Britain © The Company of Biologists Limited 2000.

Ramalho-Santos. Miguel et al., "Hedgehog signals regulate multiple aspects of gastrointestinal development," *Development 127*, pp. 2763-2772 (2000), Printed in Great Britain © The Company of Biologists Limited 2000.

Zhang, Jian et al., "Downregulation of Hedgehog Signaling Is Required for Organogenesis of the Small Intestine in *Xenopus*," *Developmental Biology*, vol. 229, pp. 188-202 (2001).

Van Den Brink, Gus R. et al., "Sonic Hedgehog Regulates Gastric Gland Morphogenesis in Man and Mouse," *Gastroenterology*, vol. 121, pp. 317-328 (2001).

Ishizuya-Oka, Atsuko et al., "Thyroid hormone-induced expression of Sonic hedgehog correlates with adult epithelial development during remodeling of the Xenopus stomach and intestine," *Differentiation*, vol. 69, pp. 27-37 (2001).

van den Brink, G.R. et al., "Sonic hedgehog expression correlates with fundic gland differentiation in the adult gastrointestinal tract," *Gut*, vol. 51, pp. 628-633 (2002).

Perron, Muriel et al., "A novel function for *Hedgehog* signaling in retinal pigment epithelium differentiation," *Development 130*, vol. 130, pp. 1565-1577, © 2003 The Company of Biologists Ltd.

Watkins, D. Neil et al., "Hedgehog signaling within airway epithelial progenitors and in small-cell lung cancer," *Nature*, vol. 422, pp. 313-317 (Mar. 20, 2003) © 2003 Nature Publishing Group.

Stenkamp, Deborah L., "Extraretinal and retinal hedgehog signaling sequentially regulate retinal differentiation in zebrafish," *Departmental Biology*, vol. 258, pp. 349-363 (2003) © 2003 Elsevier Science (USA).

Niemann, C. et al., "Indian hedgehog and β-catenin signaling: Role in the sebaceous lineage of normal and neoplastic mammalian epidermis," *PNAS*, vol. 100, Supplement 1, pp. 11873-11880 (Sep. 30, 2003).

Jarov, Artem et al., "A dual role for Sonic hedgehog in regulating adhesion and differentiation of neuroepithelial cells," *Developmental Biology*, vol. 261, pp. 520-536 (2003) © 2003 Elsevier Inc.

Allen, Mary et al., "Hedgehog Signaling Regulates Sebaceous Gland Development," *American Journal of Pathology*, vol. 163, No. 6, pp. 2173-2178 (Dec. 6, 2003) Copyright © American Society for Investigative Pathology.

Yao, Humphrey Hung-Chang et al., "Desert Hedgehog/Patched 1 signaling specifies fetal Leydig cell fate in testis organogenesis," *Genes & Development*, vol. 16, pp. 1433-1440 © 2002 by Cold Spring Harbor Laboratory Press.

Wang, Bu-er et al., "Inhibition of Epithelial Ductal Branching in the Prostate by Sonic Hedgehog Is Indirectly Mediated by Stromal Cells," *The Journal of Biological Chemistry*, vol. 278, No. 20, pp. 18506-18513 (May 16, 2003) © 2003 by the American Society for Biochemistry and Molecular Biology, Inc.

Freestone, Sarah H. et al., "*Sonic hedgehog* regulates prostatic growth and epithelial differentiation," *Developmental Biology*, vol. 264, pp. 352-362 (2003).

Berman, David M. et al. "Widespread requirement for Hedgehog ligand stimulation in growth of digestive tract tumours," *Nature*, vol. 425, pp. 846-851 (Oct. 23, 2003).

Grachtchouk, Vladimir et al., "The magnitude of hedgehog signaling activity defines skin tumor phenotype," *The EMBO Journal*, vol. 22, No. 11, pp. 2741-2751 (2003).

Zhang, Yan et al., "Hedgehog acts as a somatic stem cell factor in the *Drosophila* ovary," *Nature*, vol. 410, pp. 599-604 (Mar. 29, 2001) © 2001 Macmillan Magazines Ltd.

Outram, Susan V. et al., "Hedgehog Signaling Regulates Differentiation from Double-Negative to Double-Positive Thymocyte," *Immunity*, vol. 13, pp. 187-197 (Aug. 2000) Copyright © 2000 by Cell Press.

Keeler, Richard F., "Teratogenic Effects of Cyclopamine and Jervine in Rats, Mice and Hamsters," *Proceedings of the Society for Experimantal Biology and Medicine*, vol. 149, pp. 302-306 (1975) Copyright © 1975 by the Society for Experimental Biology and Medicine.

Keller, R.F., "Teratogenic Compounds of *Veratrum californicum* (Durand)-VI. The Structure of Cyclopamine," *Phytochemistry*, vol. 8, pp. 223-225 (1969).

Omnell, M.L. et al., "Expression of *Veratrum* Alkaloid Teratogenicity in the Mouse," *Teratology*, vol. 105-119 (1990).

Talpale Jussi et al., "Effects of oncogenic mutations in *Smoothened* and *Patched* can be reversed by cyclopamine," *Nature*, vol. 406, pp. 1005-1009 (Aug. 31, 2000) © 2000 Macmillan Magazines Ltd.

Detmer, Kristina et al., "Erythroid Differentiation in Vitro Is Blocked by Cyclopamine, an Inhibitor of Hedgehog Signaling," *Blood Cells, Molecules, and Diseases*, vol. 26, No. 4, pp. 360-372(2000) Copyright © 2000 by Academic Press.

Michimukai, Eiji et al., "Mutations in the Human Homologue of the *Drosophila* Segment Polarity Gene *Patched* in Oral Squamous Cell Carcinoma Cell Lines," *In Vitro Cellular & Developmental Biology*, vol. 37, No. 7, pp. 459-464 (Jul./Aug. 2001) ProQuest Medical Library.

Berman, David M. et al., "Medulloblastoma Growth Inhibition by Hedgehog Pathway Blockade," *Science*, vol. 297, pp. 1559-1561 (Aug. 30, 2002).

Thayer, Sarah P. et al., "Hedgehog is an early and late mediator of pancreatic cancer tumorigenesis," *Nature*, vol. 425, pp. 851-856 (Oct. 23, 2003).

Qualtrough, David et al., "Hedgehog Signalling in Colorectal Tumour Cells: Induction of Apoptosis with Cyclopamine Treatment," *Int. J. Cancer*, vol. 110, pp. 831-837 (2004) © 2004 Wiley-Liss, Inc.

Cooper, Michael K. et al., "Teratogen-Mediated Inhibition of Target Tissue Response to Shh Signaling," *Science*, vol. 280, pp. 1603-1607 (Jun. 5, 1998).

"Transient activation of B-catenin signaling in adult mouse epidermis is sufficient to induce new hair follicles but continuous activation is required to maintain hair follicle tumours," Celso et al., Development 131, 1787-1799, 2004.

Berman David M et al., *Inhibition of prostate morphogensis by the Sonic hedgehog pathway inhibitor cyclopamine*. The Journal of Urology, vol. 163, No. 4 Suppl., Apr. 2000, p. 204 XP008001018, 95th Annual Meeting of the American Urological Association, Inc.; Atlanta, Georgia, USA; Apr. 29, 2000-May 4, 1999 abstract.

Cooper MK et al., "*Teratogen-Mediated Inhibition of Target Tissue Response to Shh Signaling*", Science, vol. 280, (1998), pp. 1603-1607.

Detmer K. et al, "*Erythroid differentiation in vitro is blocked by cyclopamine, an inhibitor of hedgehog signaling.*" Developmental Biology, vol. 222 No. 1, Jun. 1, 2000, p. 242 XP008001023, Fifty-ninth Annual Meeting of the Society for Development Biology; Boulder, Colorado, USA; Jun. 7-11, 2000, ISSN: 0012-1606 abstract.

Hopyan Sevan et al, "*Indian Hedgehog and Parathyroid hormone related protein signaling in cartilage tumors of bone.*" Proceedings of the American Association for Cancer Research Annual, No. 41, Mar.

2000, p. 206 XP008001019, 91st Annual.Meeting of the American Association for Cancer Research.; San Francisco, California, USA; Apr. 1-5, 2000, Mar. 2000, ISSN: 0197-016X abstract.

Incardona JP et al., "*The teratogenic Veratrum alkaloid cyclopamine inhibits Sonic hedgehog signal transduction*", Development 125, (1998), pp. 3553-3562.

Keeler R.F. "*Teratogenic Compounds of Veratrum californicum (Durand)—VI.*", Phytochemistry, vol. 8, (1969) pp. 223-225.

Kooy AJ et al., *Expression of E-Cadherin, α- & β- Catenin, and $CD44V_6$ and the Subcellular Localization of E-Cadherin and $CD44V_6$ in Normal Epidermis and Basal Cell Carcinoma*, Human Pathology, vol. 30, No. 11, Nov. 1999, pp. 1328-1335.

Nilsson M. et al. "*Induction of basal cell carcinomas and trichoepitheliomas in mice overexpressing GLI-I*", PNAS, Mar. 28, 2000, vol. 97, No. 7, pp. 3438-3443.

Taipale et al., "*Effects of oncogenic mutations in Smoothened and Patched can be reversed by cyclopamine*", Nature, Macmillan Journals Ltd. London, GB, vol. 406, No. 6799, Aug. 31, 2000, pp. 1005-1009, XP002166408, ISSN: 0028-0836 the whole document.

Vorechovshy L. et al. "*Trichoepitheliomas Contain Somatic Mutations in the Overexpressd PTCH Gene: Support for a Gatekeeper Mechanism in Skin Tumorigenesis*", Cancer Research 57, Nov. 1, 1997, pp. 4677-4681.

Zhang Y et al., *Hedgehog acts as a somatic stem cell factor in the Drosophila ovary*, Nature vol. 410, Mar. 29, pp. 599-604, 2001.

Tas S et al, Induction of the differentiation and apoptosis of tumor cells in vivo with efficiency and selectivity. *European Journal of Dermatology* 2004; 14:96-102.

Riddle RD et al, Sonic hedgehog mediates polarizing activity of the ZPA. *Cell* 1993; 75:1401-1416.

Basler K et al, Compartment boundaries and the control of *Drosophila* limb pattern by hedgehog protein. *Nature* 1994; 368: 208-214.

Kojima T et al, Induction of a mirror-image duplication of anterior wing structures by localized hedgehog expression in the anterior compartment of *Drosophila melanogaster* wing imaginal discs. *Gene* 1994; 148:211-217.

Heberlein U et al, Growth and differentiation in the *Drosophila* eye coordinated by hedgehog. *Nature* 1995; 373: 709-711.

Lepage T et al, Signal transduction by cAMP-dependent protein kinase A in *Drosophila* limb patterning. *Nature* 1995; 373: 711-715.

Oro AE et al, Basal cell carcinomas in mice overexpressing Sonic hedgehog. *Science* 1997; 276: 817-821.

Bellusci S et al, Involvement of Sonic hedgehog (Shh) in mouse embryonic lung growth and morphogenesis. *Development* 1997; 134: 53-63.

Litingtung Y et al, Sonic hedgehog is essential to foregut development. *Nature Genetics* 1998; 20: 58-61.

Orentas DM et al, Sonic hedgehog signaling is required during the appearance of spinal cord oligodendrocyte precursors. *Development* 1999; 126:2419-2429.

Furumichi T et al, Adenosine 3':5'-cyclic monophosphate inhibits in vitro angiogenesis induced by endothelial cell growth factor. *Japanese Heart Journal* 1992; 33: 373-382.

Tsopanoglou NE et al, Opposing effects on modulation of angiogenesis by protein kinase C and cAMP-mediated pathways. *Journal of Vascular Research* 1994; 31: 195-204.

Johnson RL et al, Patched overexpression alters wing disc size and pattern: transcriptional and post-transcriptional effects on hedgehog targets. *Development* 1995; 121: 4161-4170.

deCelis JF et al, Ventral veinless, the gene encoding the Cf1a transcription factor, links positional information and cell differentiation during embryonic and imaginal development in *Drosophila melanogaster*. *Development* 1995; 121: 3405-3416.

Roberts DR et al, Sonic hedgehog is an endodermal signal inducing Bmp-4 and Hox genes during induction and regionalization of the chick hindgut. *Development* 1995; 121: 3163-3174.

Winnier G et al, Bone morphogenetic protein-4 is required for mesoderm formation and patterning in the mouse. *Genes & Development* 1995; 9: 2105-2116.

Bavik C et al, Developmental abnormalities in cultured mouse embryos deprived of retinoic acid by inhibition of yolk sac retinol binding protein synthesis. *Proceedings of the National Academy of the Sciences of USA* 1996; 93: 3110-3114.

Dickson MC et al, Defective haematopoiesis and vasculogenesis in transforming growth factor-beta 1 knock out mice. *Development* 1995; 121: 1845-1854.

D'Angelo G et al, cAMP-dependent protein kinase inhibits the mitogenic action of vascular endothelial growth factor and fibroblast growth factor in capillary endothelial cells by blocking Raf activation. *Journal of Cell Biochemistry* 1997; 6767: 353-366.

Farrington SM et al, Winged-Helix, Hedgehog and Bmp genes are differentially expressed in distinct cell layers of the murine yolk sac. *Mechanisms of Development* 1997; 62: 197-211.

St Amand TR et al, Cloning and expression pattern of chicken Pitx2: A new component in the Shh signaling pathway controlling embryonic heart looping. *Biochemical and Biophysical Research Communications* 1998; 247: 100-105.

Pepicelli CV et al, Sonic hedgehog regulates branching morphogenesis in the mammalian lung. *Current Biology* 1998; 8: 1083-1086.

Grabel L et al, Using EC and ES cell culture to study early development: recent observations on Indian hedgehog and Bmps. *International Journal of Developmental Biology* 1998; 42: 917-925.

St Jacques B et al, Indian hedgehog signaling regulates proliferation and differentiation of chondrocytes and is essential for bone formation. *Genes & Development* 1999; 13: 2072-2086.

Brown LA et al, Insights into early vasculogenesis revealed by expression of the ETS-domain transcription factor Fli-1 in wild type and mutant zebrafish embryos. *Mechanisms of Development* 2000; 90: 237-252.

Maye P et al, Indian hedgehog signaling in extraembryonic endoderm and ectoderm differentiation in ES embryoid bodies. *Mechanisms of Development* 2000; 94: 117-132.

Dyer M et al, Indian hedgehog activities hematopoiesis and vasculogenesis and can respecify prospective neuroectodermal cell fate in the mouse embryo. *Development* 2001; 128: 1717-1730.

Braybrooke JP et al, A phase II study of razoxane, an antiangiogenic topoisomerase II inhibitor, in renal cell cancer with assessment of potential surrogate markers of angiogenesis. *Clinical Cancer Research* 2000; 6: 4697-4704.

Dunn MK et al, Cyclopamine, A Steroidal Alkaloid Disrupts Development of Neural Crest Cells in Xenopus. *Developmental Dynamics* 1995; 202: 255-270.

Tas S et al, Rapid clearance of psoriatic skin lesions induced by topical cyclopamine. *Dermatology* 2004; 209: 126-131.

Sauder et al, Neovastat (AE-941), an inhibitor of angiogenesis: Randomized phase I/II clinical trial results in patients with plaque psoriasis. *J Am Acad Dermatol*; vol. 47, No. 4, 2002; 535-541.

\* cited by examiner

USE OF CYCLOPAMINE IN THE TREATMENT OF BASAL CELL CARCINOMA AND OTHER TUMORS

CROSS REFERENCE

This application is a continuation in part of PCT/TR01/00027 and a continuation-in-part of PCT/TR02/00017, both of which applications are incorporated herein by reference in their entirety.

BACKGROUND OF THE INVENTION

Basal cell carcinoma (BCC) is a common epithelial tumor. Its incidence increases with increasing age. Current treatments for BCC's include the surgical excision of the tumor together with a margin of normal tissue and, when surgery is not feasible or desirable, destruction of the tumor cells by ionizing radiation or other means. Although scarring and disfigurement are potential side effects, surgical excisions that do not leave neoplastic cells behind can provide cure. Radiation therapy acts by causing irreparably high quantity of DNA-damage which, in turn, triggers apoptotic death of the tumor cells. This mode of action of radiation-therapy, i.e. apoptosis secondary to DNA-damage, is similar to those of many chemotherapeutic agents that are currently used in the treatment of cancers. However, both radiation therapy and the cytotoxic cancer chemotherapeutics are capable of causing DNA-damage in the normal cells of patients in addition to the tumor cells. As a result, their effectivity and usefulness in cancer therapy are seriously limited. A further dilemma with the use of radiation and genotoxic cancer chemotherapeutics is the disturbing fact that, even when cure of the primary tumor is achieved, patients have markedly increased risk of developing new cancers because of the DNA-damage and the resulting mutations they have undergone during the treatment of primary tumor. Induction of apoptosis selectively in tumor cells by non-genotoxic means would therefore be most desirable in the field of cancer therapy.

BCC's frequently show inactivating mutations of the gene patched which encodes a transmembrane protein acting as a receptor for the hedgehog proteins identified first by their effect on the patterning of tissues during development. When not liganded by hedgehog, the patched protein acts to inhibit intracellular signal transduction by another transmembrane protein, smoothened. Binding of hedgehog to the patched causes relieving of this inhibition. Intracellular signal transduction by the relieved smoothened then initiates a series of cellular events resulting ultimately in alterations of the expressions of the hedgehog target genes and of cellular behaviour. General features of this hedgehog/smoothened pathway of signal transduction, first identified in *Drosophila*, are conserved in diverse living organisms from *Drosophila* to Human. However, the pathway gets more complex in more advanced organisms (e.g. presence in human of more than one genes that display significant similarity to the single patched gene of *Drosophila*). Inactivating mutations of the patched have been found to cause constitutive (ligand-free) signalling through the hedgehog/smoothened pathway. The hedgehog/smoothened pathway overactivity, resulting from mutations of the patched and/or further downstream pathway elements, is found in all BCC's. The nevoid basal cell carcinoma syndrome (NBCCS) results from patched haploinsufficiency. Patients with the NBCCS, because of an already mutant patched in all cells, develop multiple BCC's as they grow older. Hedgehog/smoothened signalling is known to be employed for normal functions in several normal tissues and for the maintenance of normal epithelial stem cells (Zhang Y et al (2001) *Nature* 410:599-604).

Cyclopamine, a steroid alkaloid, has the chemical formula shown below.

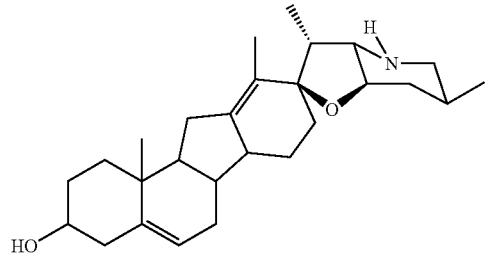

It is found naturally in the lily *Veratrum californicum* and can be obtained by purification from this and other sources. Inhibition of the hedgehog/smoothened pathway by cyclopamine has been found in chicken embryos and in cultured cells of mice. Cyclopamine has been found to inhibit the differentiation of neuronal precursor cells in developing brain (Incardona J P et al (1998) *Development* 125:3553-3562; Cooper M K et al (1998) *Science* 280:1603-1607). Studies with other differentiating cell types have also reported an inhibitory action of cyclopamine on cellular differentiation. Differentiation of bone marrow cells to erythroid cells (Detmer K. et al (2000) *Dev. Biol.* 222:242) and the differentiation of urogenital sinus to prostate (Berman D M et al (2000) *J. Urol.* 163:204) have been found to be inhibited by cyclopamine. Inhibition of hedgehog/smoothened signalling by cyclopamine has been reported to exert no significant effect on the viability of cells (Taipale J. et al (2000) *Nature* 406; 1005-1009).

SUMMARY OF THE INVENTION

This invention concerns the use of cyclopamine in vivo on basal cell carcinomas (BCC's) to achieve therapeutic effect by causing differentiation of the tumor cells and, at the same time, apoptotic death and removal of these tumor cells while preserving the normal tissue cells, including the undifferentiated cells of the normal epidermal basal layer and hair follicles. Causation of apoptosis by cyclopamine is by a non-genotoxic mechanism and thus unlike the radiation therapy and most of the currently used cancer chemotherapeutics which act by causing DNA-damage. These novel effects, previously unachieved by a cancer chemotherapeutic, make the use of cyclopamine highly desirable in cancer therapy, in the treatment of BCC's and other tumors that use the hedgehog/smoothened signal transduction pathway for proliferation and prevention of apoptosis.

In one aspect, the present invention is directed to the use of cyclopamine or a pharmaceutically acceptable salt or a derivative of cyclopamine in the topical treatment of basal cell carcinomas, particularly for the manufacture of a pharmaceutical compound for use in the topical treatment of basal cell carcinomas.

In a further aspect, the invention is directed to the use of cyclopamine or a pharmaceutically acceptable salt of cyclopamine or a derivative thereof in the treatment of basal cell carcinomas by non-topical means, including by intratumoral injections, or for the manufacture of a pharmaceutical compound for use in such a treatment.

In a further aspect, the invention is directed to the use of cyclopamine or a pharmaceutically acceptable salt of cyclopamine or a derivative of cyclopamine in the treatment of tumors that use the hedgehog/smoothened signal transduction pathway for proliferation and/or for the prevention of apoptosis or cellular differentiation, or for the manufacture of a pharmaceutical compound for use in such treatment.

BRIEF DESCRIPTION OF THE FIGURES

The patent or application file contains at least one thawing executed in color. Copies of this patent or patent application publication with color drawing(s) will be provided by the Office upon request and payment of the necessary fee.

COLOR PRINTS

Figures 1A, 1B, 1C, 1D:
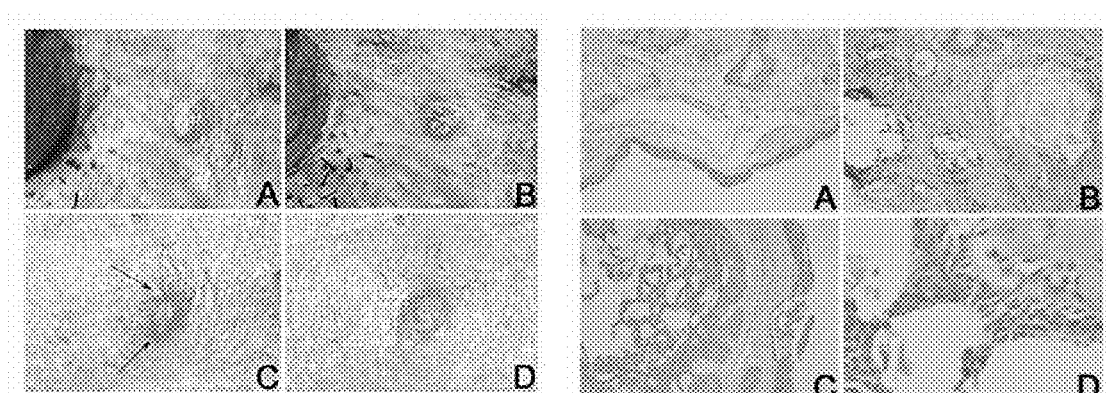
FIGS. 1A, 1B, 1C, 1D: Rapid regressions of the cyclopamine-treated BCC's as indicated by disappeared tumor regions (exemplified by arrows), markedly decreased height from skin surface and by a loss of translucency in less than a week. 1A: BCC, located on left nasolabial fold, prior to treatment. 1B: Same BCC on the fifth day of topical cyclopamine treatment. 1C: BCC, located on forehead, prior to treatment. 1D: Same BCC on the sixth day of topical cyclopamine treatment.

Color prints of the same figures as on pages 1/2 (FIGS. 1A, 1B, 1C, 1D, FIGS. 2A, 2B, 2C, 2D, 2E, 2F, FIGS. 3A, 3B, 3C, 3D, 3E, 3G, FIGS. 4A, 4B, 4C, 4D) and 2/2 (FIGS. 5A, 5B, 5C, 5D, 5E, FIGS. 6A, 6B, 6C, 6D, FIGS. 7A, 7B, 7C, 7D, 7D, 7E, 7F), added as pages 1/2a and 2/2a, respectively, because the immunohistochemical data and findings, due to their nature, can be conveyed best in color rather than in grey-scale; we respectfully request consideration of this fact by the Patent Authority and the keeping of pages 1/2a and 2/2a as part of this patent application. However, pages 1/2a and 2/2a may be removed from the patent application if it is deemed necessary by the Patent Authority.

DETAILED DESCRIPTION OF THE INVENTION

Cyclopamine was discovered as a teratogenic compound of *Veratrum* plants (Keeler R. F. (1969) *Phytochemistry* 8:223-225). It has been reported to inhibit differentiation of the precursors of the ventral cells in the developing brain (Incardona J. P. et al (1998) *Development* 125:3553-3562; Cooper M. K. et al. (1998) *Science* 280:1603-1607). Inhibition of cellular differentiation by cyclopamine has been reported in other systems as well, including the differentiation of bone marrow cells to erythroid cells (Detmer K. et al (2000) *Dev. Biol.* 222-242) and the differentiation of urogenital sinus to prostate (Berman D. M. et al (2000) *J. Urol.* 163-204). However, the opposite was found to be true in this invention with the tumor cells exposed to cyclopamine. Along with the cyclopamine-induced differentiation of tumor cells, apoptosis of tumor cells was also induced. Induction of tumor cell apoptosis by cyclopamine, again previously undescribed, is shown to be highly efficient. Furthermore, induction of apoptosis by cyclopamine was not secondary to a genotoxic effect and had extreme specificity; even the outer root sheath cells of hair follicles and normal epidermis basal cells that were adjacent to the tumor cells were well preserved while the tumor cells had differentiated and were undergoing apoptosis. Lack of adverse effects of the described treatment is confirmed also by the presence of clinically normal-looking healthy skin and hair at the sites of cyclopamine application in patients (longest duration of follow-up of a human subject is over 31 months at the time of writing and shows safety of the treatment also in the long term). Above summarised features of the treatment described in this invention make it highly desirable in cancer therapy and provide solutions to the long-standing problems of cancer therapy.

It is specifically contemplated that molecules can be derived from cyclopamine or synthesised in such a way that they possess structural features to exert similar receptor binding properties and biological/therapeutic effects as cyclopamine. Such a molecule is called here a "derivative of cyclopamine" and defined as follows: A molecule that contains the group of atoms of the cyclopamine molecule required for the binding of cyclopamine to its biological target but contains also modifications of the parent cyclopamine molecule in such ways that the newly derived molecule continues to be able to bind specifically to the same biological target to exert the biological effects of cyclopamine disclosed herein. Such modifications of cyclopamine may include one or more permissible replacement of or a deletion of a molecular group in the cyclopamine molecule or addition of a molecular group (particularly a small molecular group such as the methyl group) to the cyclopamine molecule, provided that the resultant molecule is stable and possesses the capability of specific binding to the same biological target as cyclopamine to exert the biological effects described herein. Derivation of such new molecules from cyclopamine can be readily achieved by those skilled in the art and the possession or lack of the biological effects of cyclopamine in the newly derived molecule can also be readily determined by those skilled in the art by testing for the biological effects disclosed herein.

For topical applications, cyclopamine can be dissolved in ethanol or another suitable solvent and mixed with a suitable base cream, ointment or gel. Cyclopamine may also be entrapped in hydrogels or in other pharmaceutical forms enabling controlled release and may be adsorbed onto dermal patches. In a pharmaceutical composition for topical administration, the cyclopamine or a salt or derivative thereof should be present in a concentration of 0.001 mM to 100 mM, preferably 12 to 24 mM. The effects shown in FIG. 1A to FIG. 1D, FIG. 2A to FIG. 2F, FIG. 3A to FIG. 3G and FIG. 4A to FIG. 4D have been obtained by a cream preparation obtained by mixing a solution of cyclopamine in ethanol with a base cream, so as to get a final concentration of 18 mM cyclopamine in cream. The base cream used is made predominantly of heavy paraffin oil (10% w/w), vaseline (10% w/w), stearyl alcohol (8% w/w), polyoxysteareth-40 (3% w/w) and water (68% w/w), but another suitably formulated base cream is also possible. Optimal concentration of cyclopamine in a pharmaceutical form as well as the optimal dosing and application schedules can obviously be affected by such factors as the particular pharmaceutical form, the localisation and characteristics of the skin containing the tumor (e.g. thickness of the epidermis) and the tumor size; however these can be determined by following well known published optimisation methods. The dosing and the application schedules followed for the tumors shown in FIG. 1A (BCC on the nasolabial fold, about 4×5 mm on surface) and FIG. 1C (BCC on the forehead, about 4×4 mm on surface) are as follows: 10±2 μl cream (containing 18 mM cyclopamine) applied directly onto the BCC's with the aid of a steel spatula four times per day, starting about 9.00 a.m. with about 3½ hours in between. Night-time applications, avoided in this schedule because of possible loss of cream from the patient skin to linens during sleep, can be performed by suitable dermal patches. Preservation of the undifferentiated cells in the normal epidermis and in hair follicles following exposure to cyclopamine, as described in this invention, provide information about the tolerable doses in other possible modes of administration as well; e.g. direct intratumoral injection of an aqueous solution or systemic administration of the same or of cyclopamine entrapped in liposomes.

FIG. 1A, FIG. 1B, FIG. 1C and FIG. 1D show rapid clinical regressions of the BCC's following exposure to cyclopamine. Besides the visual disappearance of several tumor areas within less than a week of cyclopamine exposure, there is a loss in the typically translucent appearance of the BCC's as seen by the comparison of FIG. 1B to FIG. 1A and of FIG. 1D to FIG. 1C.

FIG. 2A to FIG. 2F show microscopic appearances of the tumor areas subjected to surgical excisions together with a margin of normal tissue on the fifth and sixth days of cyclopamine applications when the BCC's had lost most of their pre-treatment areas but still possessed few regions that, although markedly decreased in height, had not yet completely disappeared and therefore had residual tumor cells for microscopic analyses.

Figures 2A, 2B, 2C, 2D, 2E, 2F:
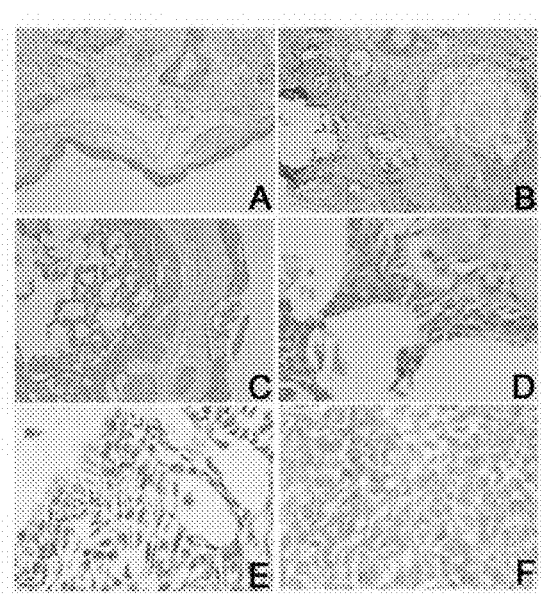
FIGS. 2A, 2B, 2C, 2E, 2F: Microscopic appearances of the cyclopamine- and placebo-treated BCC's, showing the cyclopamine-induced massive apoptotic death and removal of the tumor cells and the disappearance of tumor nodules to leave behind cystic spaces with no tumor cells. Skin areas corresponding to the pre-treatment positions of the BCC's were excised surgically on the fifth and sixth days of cyclopamine exposure with a margin of normal tissue and subjected to conventional fixation, sectioning and hermatoxylene-eosine staining for microscopic analyses. 2A: Large cyst in the dermis corresponding to the position of a disappeared tumor nodule showing no residual tumor cells. 2B: Similar cysts in another dermal area that contained BCC prior to, but not after, treatment with cyclopamine. 2C: Low power view of an area of the BCC shown on FIG. 1D showing residual cells and formation of a large cyst by the joining together of the numerous smaller cysts in between these cells. 2D: High power view from an interior region of the same residual BCC as in FIG. 2C showing greatly increased frequency of the apoptotic cells and the formation as well as enlargement of the cysts by the apoptotic removal of the BCC cells. 2E: High power view from a peripheral region of the same residual BCC as in FIG. 2C also showing greatly increased frequency of the apoptotic cells and the formation of cysts by the apoptotic removal of BCC cells. 2F: High power view from an internal area of a placebo-treated BCC showing typical neoplastic cells of this tumor and the absence of apoptosis. Original magnifications are 100× for 2A, 2B, 2C and 1000× for 2D, 2E, 2F.

FIG. 2A and FIG. 2B show, on tissue sections, the skin areas corresponding to the visually disappeared tumor nodules. The tumors are seen to have disappeared to leave behind large cystic structures containing little material inside and no detectable tumor cells.

FIG. 2C shows microscopic appearance of a skin area that contained still visible BCC in vivo. These regions are seen to contain residual BCC's displaying large cysts in the tumor center and smaller cystic structures of various sizes located among the residual BCC cells towards the periphery.

FIG. 2D and FIG. 2E show 1000× magnified appearances from the interior and palisading peripheral regions of these residual BCC's and show the presence of massive apoptotic activity among the residual BCC cells regardless of the tumor region. These high magnifications show greatly increased frequency of the BCC cells displaying apoptotic morphology and formation of the cystic structures by the apoptotic removal of cells, as exemplified in FIG. 2D by the imminent joining together of the three smaller cysts into a larger one upon removal of the apoptotic septal cells.

FIG. 2F shows that the BCC's treated with the placebo cream (i.e. the cream preparation identical to the cyclopamine cream except for the absence of cyclopamine in placebo) show, by contrast, the typical neoplastic BCC cells and no detectable apoptotic activity.

Cells undergoing apoptosis are known to be removed by macrophages and by nearby cells in normal tissues and the quantification of apoptotic activity by morphological criteria on hematoxylene-eosine stained sections is known to provide an underestimate. Despite these, the quantitative data shown in Table 1 show greatly increased apoptotic activity caused by cyclopamine among the residual BCC cells.

Figures 3A, 3B, 3C, 3D, 3E, 3F, 3G:
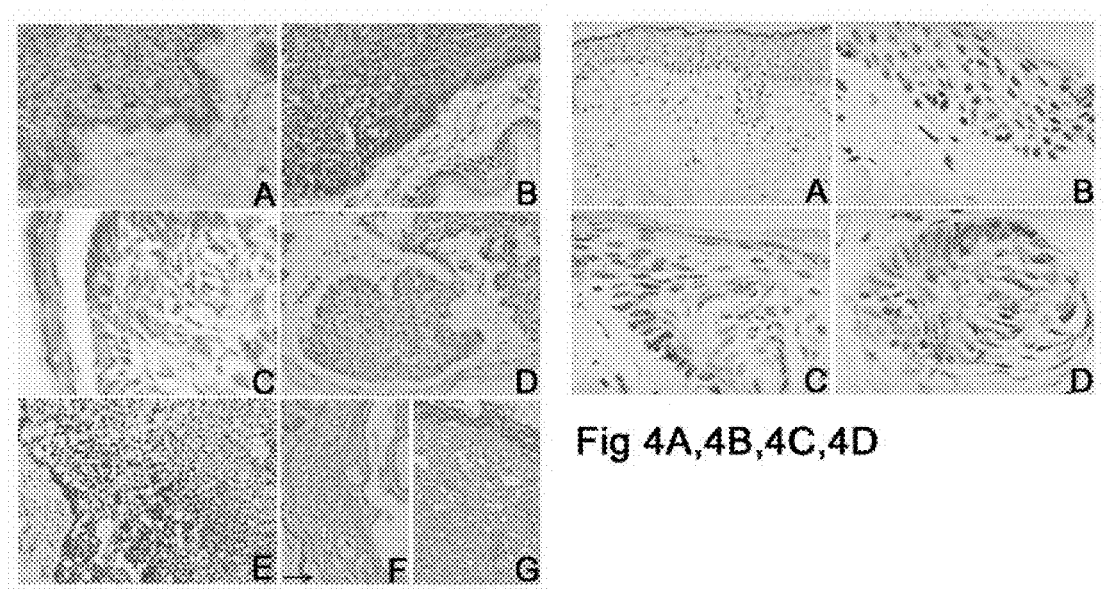
FIGS. 3A, 3B, 3C, 3E, 3F, 3G: Immunohistochemical analyses of the cyclopamine- and placebo-treated BCC's showing differentiation of all residual BCC cells under the influence of cyclopamine and the decrease of p53 expression in BCC's following exposure to cyclopamine. 3A and 3B: Absence of staining with the monoclonal antibody Ber-Ep4 in all residual cells of cyclopamine-treated BCC (3A) contrasted with the strong staining in placebo-treated BCC (3B) showing that all residual cells in the cycopamine-treated BCC's are differentiated to or beyond a step detected by Ber-Ep4. Ber-Ep4 is a known differentiation marker that stains the BCC cells as well as the undifferentiated cells of the normal epidermis basal layer and of hair follicles but not the differentiated upper layer cells of normal epidermis. 3C: Heterogenous labelling of the residual cells of a cyclopamine-treated BCC with the *Ulex Europaeus* lectin type 1 showing differentiation of some of the BCC cells all the way to the step detected by this lectin which normally does not label the BCC's or the basal layer cells of the normal epidermis but labels the differentiated upper layer cells. 3D and 3E: Decreased expression of p53 as detected by the monoclonal antibody DO-7 in cyclopamine-treated BCC's (3) in comparison to the placebo-treated BCC's (3E). Expression of p53 is known to decrease upon differentiation of the epidermal basal cells and upon differentiation of cultured keratinocytes. It is also well known that the amount of p53, detectable by DO-7, increases in cells when they are exposed to DNA-damaging agents. 3F and 3G: Consistent retraction of BCC's from stroma, which is a feature known to be associated with the arrest of tumor cell proliferation, seen in cyclopamine-treated (3F, arrow shows the retraction space) but not in placebo-treated (3G) tumors (difference of the cyclopamine- and placebo-treated BCC's in terms of retraction from stroma is seen also in 3D, 2C vs 3B, 3E). Original magnifications are 400× for 3A, 3B, 3D, 3E, 1000× for 3C and 100× for 3F, 3G. All immunohistochemical labellings are with peroxidase-conjugated streptavidin binding to biotinylated secondary antibody; labelling is indicated by the brown-coloured staining. Sections shown in 3F and 3G are stained with Periodic Acid-Schiff and Alcian blue.

The loss of translucency in the cyclopamine-treated BCC's raises the intriguing possibility of differentiation of BCC's under the influence of cyclopamine. This possibility, which can be tested by immunohistochemical analyses of the BCC's, is found to be the case in this invention. In normal, epidermis, differentiation of basal layer cells to the upper layer cells is accompanied by a loss of labelling with the monoclonal antibody Ber-Ep4. Ber-Ep4 labels also the BCC cells and is a known marker for these neoplasms. FIG. 3A, FIG. 3B and the quantitative data on Table 1 show that, while Ber-Ep4 strongly labels all peripheral palisading cells and over 90% of the interior cells of the placebo-treated BCC's, none of the residual peripheral or interior cells of the cyclopamine-treated BCC's are labelled by Ber-Ep4. Differentiation of the BCC's under the influence of cyclopamine, hitherto unknown by any other means and highly unusual because of achievement of it in vivo and in all cells by immunohistochemical criteria, has independent value in the treatment of cancer.

Another differentiation marker, *Ulex Europeaus* lectin type 1, normally does not label the BCC's or the basal layer cells of normal epidermis but labels the differentiated upper layer cells. FIG. 3C, showing the heterogenous labelling of the residual cells of cyclopamine-treated BCC's with this lectin, shows differentiation of some of the BCC cells beyond the differentiation step detected by Ber-Ep4 all the way to the step detected by *Ulex Europeaeus* lectin type 1.

The p53 is a master regulator of the cellular response to DNA-damage. Amount of this protein is known to increase in the cell nucleus following exposure of cells to genotoxic agents. When the DNA-damage is increased beyond a threshold, p53 serves for the apoptotic death of cells. Radiation therapy of cancer and the genotoxic cancer chemotherapeutics that are currently common, act largely by this mechanism, i.e. by causation of apoptosis secondary to the damaging of DNA. The monoclonal antibody DO-7 can bind both normal and missense mutant (i.e. non-functional) forms of p53 and is known to be capable of detecting the increase of p53 in the cells following exposure to DNA-damaging agents.

FIG. 3D, FIG. 3E and the quantitative data in Table I show that both the DO-7 labelling intensity and the frequency of labelled cells are markedly decreased in cyclopamine-treated BCC's in comparison to the placebo-treated BCC's. Thus cyclopamine causes, not an increase, but rather a decrease of p53 in the nuclei of cyclopamine-treated BCC cells. Since expression of p53 is known to decrease in epidermal cells upon differentiation, the decreased DO-7 labelling of the cyclopamine-treated BCC's is likely to be secondary to the cyclopamine-induced differentiation of the BCC cells. In any case, massive apoptotic activity in the cyclopamine-treated BCC's despite markedly decreased p53 expression means that the cyclopamine-induced apoptosis of these tumor cells is by a non-genotoxic mechanism.

Arrest of the proliferation of BCC's is known to be associated with their retraction from stroma. Although retraction from stroma can also be caused artefactually by improper fixation and processing of the tissues, adherence to published technical details ensures avoidance of such artefacts. As shown in FIG. 3F and FIG. 3G, cyclopamine-treated, but not placebo-treated BCC's, are consistently retracted from stroma. Exposure of BCC's to cyclopamine thus appears to be associated also with an arrest of proliferation.

Figures 4A, 4B, 4C, 4D:
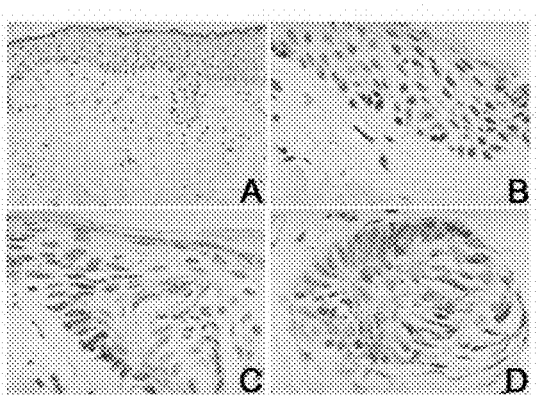
FIGS. 4A, 4B, 4C, 4D: Normal pattern of labelling of the cyclopamine-treated normal skin with Ber-Ep4 showing that the undifferentiated cells of normal epidermis and of hair follicles are preserved despite being exposed to the same schedule and doses of cyclopamine as the BCC's. 4A: Ber-Ep4 labelling of the basal layer cells of the epidermis treated with cyclopamine. 4B and 4C: Higher power views from different areas of cyclopamine-treated epidermis showing Ber-Ep4 labelling of the basal cells. 4D: High power view of a hair follicle treated with cyclopamine yet showing normal labelling with Ber-Ep4. Original magnification is 400× for 4A and 1000× for 4B, 4C, 4D. Immunohistochemical detection procedure is the same as in FIGS. 3A, 3B; labelling is indicated by brown coloring.

FIG. 4A to FIG. 4D show Ber-Ep4 labelling of the normal skin tissue found on and around the cyclopamine-treated BCC's. Different epidermal areas that were treated with cyclopamine are seen in FIG. 4A, FIG. 4B and FIG. 4C to display normal pattern of labelling with Ber-Ep4, i.e. labelling of the basal layer cells. Similarly, FIG. 4D shows normal Ber-Ep4 labelling of a hair follicle exposed to cyclopamine. Histological and immunohistochemical examinations of the cyclopamine-treated skin using antibodies to cytokeratin 15 and cytokeratin 19 (known to label the hair follicle outer root sheath cells with stem cell features) also revealed normal staining of hair follicles and revealed no adverse effect of the treatment on tissues and putative stem cells. Thus, the undifferentiated cells of normal epidermis and of hair follicles are preserved, despite being exposed to the same schedule and doses of cyclopamine as the BCC's. Further relevant in this regard is the display of normal skin and hair in the followed-up former treatment areas (as long as over 31 months at this writing) implying a lack of adverse effects also functionally.

Causation of highly efficient differentiation and apoptosis of the tumor cells in vivo by cyclopamine at doses that preserve the undifferentiated tissue cells are hitherto unknown achievements that, together with the non-genotoxic mode of action of cyclopamine, support the use of cyclopamine not only on BCC's but also on those internal tumors that utilize the hedgehog/smoothened pathway for proliferation and for prevention of apoptosis and/or differentiation.

Figure 5A:
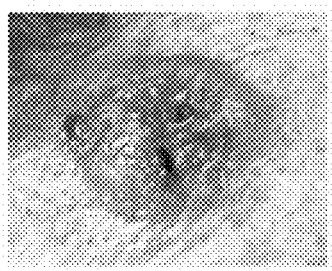
FIG. 5A shows an ulcerated BCC in the upper nasal region of a 68-year old man prior to treatment.
Figure 5B:
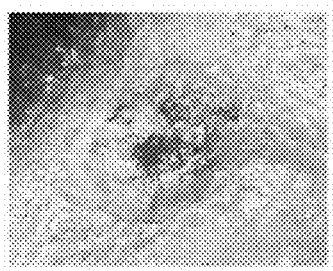
FIG. 5B shows the same BCC as in FIG. 5A at the 54$^{th}$ hour of cyclopamine application to its lower half.
Figure 5C:
FIG. 5C shows a section from the cyclopamine-applied half of the BCC at the 54$^{th}$ hour. Hematoxylene-Eosine (H&E) staining, 400× original magnification.
Figure 5D:
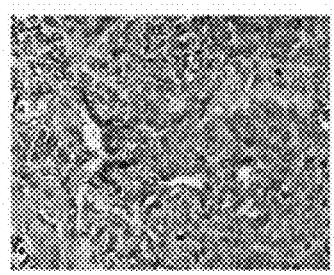
FIG. 5D shows a section from the untreated region of the same BCC, H&E, 400× original magnification.
Figure 5E:
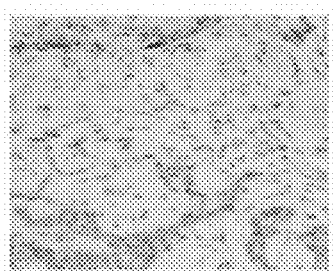
FIG. 5E shows a section from the cyclopamine applied half of the BCC at the 54$^{th}$ hour with immunohistochemical staining for the Ki-67 antigen. 200× original magnification.
Figure 5F:
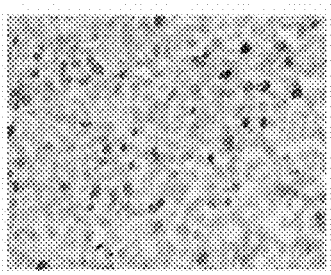
FIG. 5F shows a section from the untreated region of the same BCC with immunohistochemical staining for the Ki-67 antigen. 200× original magnification.

FIG. 5A shows a large ulcerated BCC on the upper nasal region of a 68-year old man prior to treatment. Cyclopamine cream (18 mM in the base cream described above) was applied to the lower half of the BCC shown in FIG. 5A. Every third hour, about 20 µl cream was applied directly onto the lower half and the upper half was left untreated. Thus, the tumor cells in the uppermost part (FIG. 5A) are least likely to receive cyclopamine by possible diffusion form the directly applied region and will be exposed to relatively much lower concentrations of cyclopamine, if any. FIG. 5B shows the tumor on the $54^{th}$ hour of treatment just prior to surgical excision for investigation. While rapid regression of the tumor is evident in the cyclopamine-applied lower half, the region of the tumor furthest away from the directly applied half is seen to be relatively unaltered (FIG. 5B; the region towards the upper right corner of figure). FIG. 5C shows a hematoxylene-eosine stained section from the lower (cyclopamine-treated) part of the excised tissue. Numerous apoptic cells are seen together with variously sized cysts that form as a result of the death and removal of the tumor cells (FIG. 5C). In contrast, the non-treated region of the same tumor furthest away from the cyclopamine-applied half shows a solid tumor tissue with mitotic figures and no detectable apoptotic cells (FIG. 5D). FIG. 5E and FIG. 5F show the immunohistochemically stained tissue sections from the cyclopamine-treated and non-treated regions, respectively, of the tumor using the monoclonal antibody Ki-S5 (Dako A/S, Glostrup, Denmark) against the Ki-67 antigen. The Ki-67 antigen, which is a known marker of the proliferating cells, is no longer expressed in the cyclopamine-treated region of the tumor (FIG. 5E), while the tumor furthest away from the cyclopamine-applied region clearly display proliferative activity (FIG. 5F). Thus staining of the tissue sections with an antibody against the Ki-67 antigen shows again arrest of tumor cell proliferation by cylopamine under the conditions described.

Figure 6A:
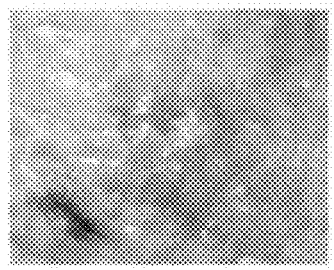
FIG. 6A shows a trichoepithelioma on the cheek of an 82-year old man prior to treatment.
Figure 6B:
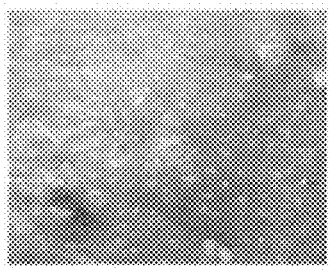
FIG. 6B shows the same skin region as in FIG. 6A after 24 hours of treatment with cyclopamine.
Figure 6C:
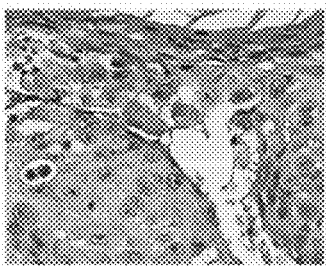
FIG. 6C shows a section from the excised skin region shown in FIG. 6B with residual tumor cells. H&E, 400× original magnification.
Figure 6D:
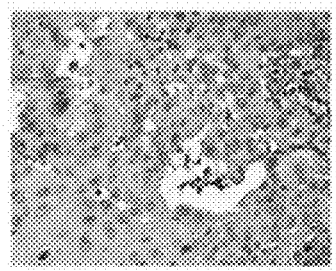
FIG. 6D shows another area from the same tissue as in FIG. 6C. In addition to the numerous apoptotic cells and the formation of cystic structures by their removal, the tumor is seen to be infiltrated by mononuclear cells. H&E, 200× original magnification.

Trichoepithelioma is another tumor associated with genetic changes that cause increased hedgehog-smoothened signalling (Vorechovsky L. et al. (1997) *Cancer Res.* 57:4677-4681; Nilsson M. et al. (2000) *Proc. Natl. Acad. Sci. USA* 97:3438-3443). FIG. 6A shows a trichoepithelioma on the cheek of an 82-year old man prior to treatment and FIG. 6B shows the same skin area after only 24 hours of exposure to the cyclopamine cream (18 mM cyclopamine in the base cream; about 25 µl cream was applied every third hour directly onto the tumor). Because of the rapid regression, treatment was discontinued on the $24^{th}$ hour and the entire skin area corresponding to the original tumor was excised for investigation. FIG. 6C and FIG. 6D show the tissue regions that contained residual tumor cells on the $24^{th}$ hour and reveal marked apoptotic activity among these residual tumor cells. Cystic spaces resulting from the apoptotic removal of tumor cells (FIG. 6C, FIG. 6D) as well as mononuclear cellular infiltration of tumor (FIG. 6D) are seen. Another noteworthy finding in this patient was the decreased size and pigmentation of a mole located nearby the treated tumor on the $24^{th}$ hour of treatment (FIG. 6B versus FIG. 6A). As cyclopamine could have diffused from the adjacent area of application, the mole (a benign melanocytic tumor) appears to be sensitive to relatively low concentrations of cyclopamine. Indeed, treatment of melanocytic nevi with the cyclopamine cream (18 mM cyclopamine in base cream) in another volunteer also caused similarly rapid depigmentation and disappearance of the nevi (data not shown). Thus, the invention is also suitable for cosmetic purposes, e.g. decreasing pigmentation in the hyperpigmented skin areas and lesions and improving the appearance of such skin areas.

Figure 7A:
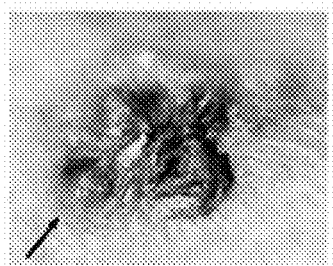
FIG. 7A shows a pigmented BCC in the lower eyelid of a 59-year old man prior to treatment.
Figure 7B:
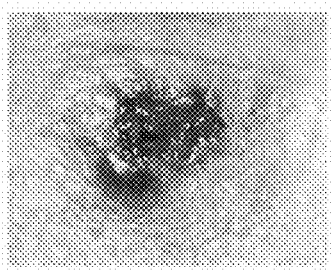
FIG. 7B shows the same BCC as in FIG. 7A on the third day of treatment with cyclopamine.
Figure 7C:
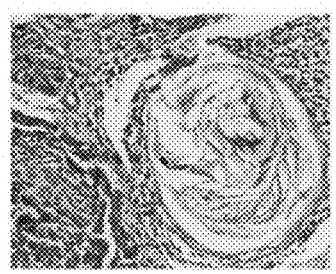
FIG. 7C shows a section from the treated region of the BCC shown in FIG. 7B, H&E, 200× original magnification.
Figure 7D:
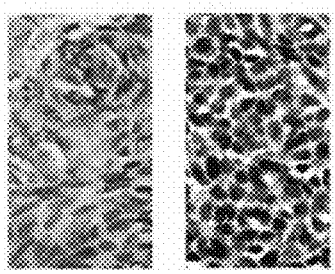
FIG. 7D shows a close up view of an area of residual tumor cells in a section from the treated region of the BCC shown in FIG. 7B, H&E, 400× original magnification.
Figure 7E:
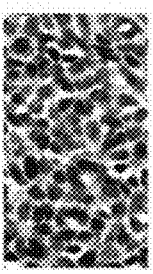
FIG. 7E shows a section from a punch biopsy material obtained from the BCC shown in FIG. 7A prior to treatment, H&E, 400× original magnification.

FIG. 7A shows a pigmented BCC on the lower eyelid of a 59-year old man prior to treatment. Cyclopamine cream (18 mM cyclopamine in the base cream) was applied in this patient onto all of the nodules except for the one marked by the arrow. This nodule, which could have received cyclopamine only by diffusion from the adjacent treated region, would be exposed to a relatively lower concentration of cyclopamine. As the pigmented nature of this tumor facilitated clinical follow-up, treatment (application of about 20 cyclopamine cream, 18 mM cyclopamine in base cream, on every fourth hour) was discontinued on the third day when the tumor in the treated region had largely regressed but still contained visible parts (FIG. 7B). The tumor was then followed up without treatment for a study of the possible late effects. A clear further clinical regression was not observed in the absence of treatment and the skin area corresponding to the original tumor was excised on the sixth day of follow-up (ninth day from the start of treatment). Hematoxylene-eosine stained sections from the treated region of tumor revealed many cystic spaces that lacked tumor cells (FIG. 7C). The absence of an epithelium lining these cysts (FIG. 7C) is consistent with the representation by these cysts of the tissue areas that were formerly occupied by the tumor cells. At this time point (the sixth day of non-treated follow-up), tissue sections displayed a relative paucity of the apoptotic cells (FIG. 7C) consistent with the known rapidity of the clearance of apoptotic cells from live tissues. On the other hand, the residual tumor cells, particularly near the edges of cysts, showed unusually high frequencies of cells displaying features of spinous differentiation (e.g. the area towards the lower left of FIG. 7C; seen more clearly on higher magnification as exemplified from another area in FIG. 7D). Similar areas of differentiation or cysts were absent in the punch biopsy material obtained from the same tumor prior to the initiation of treatment (FIG. 7E). Other markers of differentiation also revealed induction of the differentiation of tumor cells by the treatment with cyclopamine. For example expression of the cell adhesion molecule CD44 is known to increase upon differentiation of the epidermal basal cells to the upper spinous layer cells (Kooy A J et al (1999) *Human Pathology* 30:1328-1335). We found weak, patchy and low frequency CD44 labelling in the punch biopsy material obtained from this BCC prior to the initiation of treatment and also in other untreated BCC's whereas the cyclopamine-treated BCC's exhibited markedly increased, strong labelling of essentially all residual tumor cells [labelling was with anti-human CD44 antibody F10-44-2 to the CD44 standard (Novocastra Labs Ltd, U.K.); data not shown].

Figure 7F:
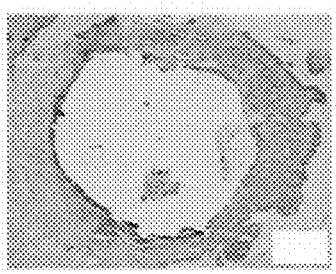
FIG. 7F shows a section containing part of the BCC nodule marked by the arrow in FIG. 7A. Cyclopamine cream was not applied directly onto this nodule but cyclopamine could have diffused from the adjacent direct application area (left of the figure). The tissue was excised after 3 days of treatment and 6 days of non-treated follow-up. Immunohistochemical labelling with Ber-Ep4. Notice a gradient pattern of the Ber-Ep4 labelling in the direction of the diffusion of cyclopamine. 100× original magnification.

The tumor nodule (marked by arrow in FIG. 7A) onto which we did not apply cyclopamine but could have received relatively lower concentrations by diffusion from the nearby application area, showed a large cystic center on the sixth day of follow-up (FIG. 7F). Immunohistochemical labelling of the sections through this nodule with Ber-Ep4 demonstrated a remarkable dose-response effect for the cyclopamine-induced differentiation of tumor cells (FIG. 7F; notice the absence of Ber-Ep4 labelling in the region of nodule towards the cyclopamine application area and the labelling in the region away from cyclopamine application). Importantly, it is also seen that the tumor cells that had differentiated beyond a critical step under the influence of cyclopamine (the Ber-Ep4 (−) cells on the side towards the area of cyclopamine application) had not reverted during the six days of non-treated follow-up. Thus while the tumor response to optimal concentrations of cyclopamine was rapid, suboptimal concentrations could not induce the differentiation (and apoptosis) of tumor cells.

These examples illustrate effectiveness of the described treatment in the causations of tumor cell differentiation and apoptosis and in obtaining rapid clinical regression of the tumors displaying hedgehog/smoothened signalling. Effectiveness on several independent tumors in unrelated patients with differing genotypes is consistent with the general utility of the described treatment.

Of the numerous substances known in the art to display inhibitory activity on tumor cell proliferation, only a small minority prove to be usable or effective in the treatment of tumors in patients. A major reason for this is the causation of harm also to the normal cells (particularly to the progenitor and stem cells) and the development of intolerable adverse effects. As hedgehog/smoothened signalling is well known to be employed by several normal cell types and for the maintenance of stem cells (Zhang Y et al (2001) *Nature* 410:599-604), use of cyclopamine on tumors of patients would have been anticipated to lead to adverse effects, especially on the normal tissues around tumors that are exposed to the same schedule and doses of cyclopamine as the tumors. However, treatment with cyclopamine under the described conditions has not revealed undue adverse effects on normal tissue components (including the putative stem cells) by histological/immunohistochemical criteria. Moreover, former skin sites of cyclopamine application that have been followed up more than 31 months at the time of this writing continue to display healthy-looking normal skin and hair, suggesting functional preservation as well of the stem cells and long-term safety. Our finding that a transient exposure to cyclopamine can suffice for the causations of tumor cell differentiation and apoptosis is further surprising and facilitates treatment of internal tumors as well. The term transient administration of cyclopamine for treatment as used here means administration of cyclopamine for a period that is short enough so that causation of the apoptosis and/or differentiation of the normal tissue cells do not happen to such an extend to lead to intolerable adverse effects. We describe in this invention that tumor cells can be caused to undergo apoptosis and/or differentiation in vivo much faster than normal tissue cells so that during the same period of exposure to cyclopamine relatively much smaller proportion or no normal tissue cells undergo cyclopamine-induced apoptosis and/or differentiation, making thereby the clinically detectable or intolerable adverse effects minimal or nonexistent. It is also clear that the therapeutic effectiveness described herein and the rapid disappearance of treated tumors could not be possible without the causation of tumor cell apoptosis since merely inhibiting or slowing the tumor cell proliferation by cyclopamine would, at best, help one only to keep the tumor at its pre-treatment size.

TABLE 1

Induction of the Differentiation and Apoptosis of Basal Cell Carcinoma Cells by Topical Cyclopamine

| | Peripheral Palisading Cells of the BCCs Treated with | | Non-Palisading Cells of the BCCs Treated with | |
|---|---|---|---|---|
| | Placebo | Cyclopamine | Placebo | Cyclopamine |
| % of Cells showing ≦ 2 Morphological Signs of Apoptosis on H & E Stained Tissue Sections | 0 ± 0 | 20 ± 8 | 0.2 ± 0.4 | 18 ± 11 |
| % of Cells Labelled with Ber-Ep4 | 100 ± 0 | 0 ± 0 | 91 ± 8 | 0 ± 0 |
| % of Cells Labelled with DO-7 | 58 ± 27 | 16 ± 11 | 67 ± 22 | 5 ± 3 |

Means ± standard deviations from at least 16 randomly selected high-power (1000 X) fields of the tissue sections of each tumor group are shown. p < 0.001 for the placebo vs. cyclopamine-treated tumors for all the parameters, both for the palisading peripheral and the non-palisading (interior) tumor areas.

The invention claimed is:

1. A method for inducing apoptosis of tumor cells in a tumor-bearing patient, comprising
   determining that Hedgehog/Smoothened signaling is utilized for inhibition of apoptosis of tumor cells and
   administering to the patient cyclopamine or a pharmaceutically acceptable salt thereof in a dose that is sufficient to induce apoptosis of said tumor cells and to cause decrease of size or disappearance of the tumor.

2. A method for treatment of a patient having a tumor wherein Hedgehog/Smoothened signaling is utilized for inhibition of apoptosis of the tumor cells, comprising
   administering to the patient a medicament comprising cyclopamine or another compound that selectively inhibits Hedgehog/Smoothened signaling,
   wherein said medicament is administered in a dose that is sufficient to induce apoptosis of said tumor cells and causes decrease of size or disappearance of the tumor.

3. The method according to claim 2, characterized in that a dose sufficing to induce apoptosis of the tumor cells causes a smaller proportion of normal tissue cells or no normal tissue cells to undergo apoptosis.

4. A method for treatment of a patient having a tumor wherein Hedgehog/Smoothened signaling is utilized for inhibition of differentiation and for inhibition of apoptosis of tumor cells, comprising
   administering to the patient a medicament comprising cyclopamine or another compound that selectively inhibits Hedgehog/Smoothened signaling,
   wherein said medicament is administered in a dose that is sufficient to induce differentiation and apoptosis of said tumor cells and causes decrease of size or disappearance of the tumor.

5. The method according to claim 4, characterized in that a dose sufficing to induce differentiation and apoptosis of the tumor cells causes a smaller proportion of normal tissue cells or no normal tissue cells to undergo differentiation and apoptosis.

6. The method according to any one of claims 2 to 5, wherein said another compound that selectively inhibits Hedgehog/Smoothened signaling is a compound that binds to the same biological target as cyclopamine to exert said inhibition.

7. The method according to any one of claims 2 to 5, wherein said another compound that selectively inhibits Hedgehog/Smoothened signaling is a derivative of cyclopamine.

8. The method according to any one of claims 2 to 5, wherein said medicament is a pharmaceutical composition selected from the group of compositions for topical, non-topical or systemic administration.

9. The method according to claim 8, characterized in that the composition for non-topical or systemic administration is in the form of an aqueous solution.

10. The method according to claim 8, characterized in that the composition for non-topical or systemic administration is in the form of liposomes, having cyclopamine or said another compound entrapped therein.

11. The method according to claim 8, characterized in that the non-topical administration is direct intratumoral injection.

12. The method according to claim 8, characterized in that cyclopamine or said another compound is in a pharmaceutical form enabling controlled release.

13. The method according to claim 8, characterized in that cyclopamine or said another compound is adsorbed onto a dermal patch.

14. The method according to claim 8, characterized in that said medicament is in the form of a cream or ointment or a gel or a hydrogel.

15. A method for treatment of a human subject having a tumor wherein Hedgehog/Smoothened signaling is utilized for inhibition of apoptosis of the tumor cells, comprising administering to the subject a medicament comprising cyclopamine or another compound that selectively inhibits Hedgehog/Smoothened signaling, wherein said medicament is administered in a dose that is sufficient to induce apoptosis of said tumor cells and causes decrease of size or disappearance of the tumor.

16. A method for treatment of a human subject having a tumor wherein Hedgehog/Smoothened signaling is utilized for inhibition of apoptosis of the tumor cells, comprising administering to the subject a medicament comprising cyclopamine or another compound that inhibits Hedgehog/Smoothened signaling by binding to the same biological target to which cyclopamine binds to inhibit Hedgehog/Smoothened signaling, wherein said medicament is administered in a dose that is sufficient to induce apoptosis of said tumor cells and causes decrease of size or disappearance of the tumor.

17. A method for treatment of a human subject having a tumor wherein Hedgehog/Smoothened signaling is utilized for inhibition of differentiation and for inhibition of apoptosis of the tumor cells, comprising administering to the subject a medicament comprising cyclopamine or another compound that selectively inhibits Hedgehog/Smoothened signaling, wherein said medicament is administered in a dose that is sufficient to induce differentiation and apoptosis of said tumor cells and causes decrease of size or disappearance of the tumor.

18. A method for treatment of a human subject having a tumor wherein Hedgehog/Smoothened signaling is utilized for inhibition of differentiation and for inhibition of apoptosis of the tumor cells, comprising administering to the subject a medicament comprising cyclopamine or another compound that inhibits Hedgehog/Smoothened signaling by binding to the same biological target to which cyclopamine binds to inhibit Hedgehog/Smoothened signaling, wherein said medicament is administered in a dose that is sufficient to induce differentiation and apoptosis of said tumor cells and causes decrease of size or disappearance of the tumor.

19. A method according to claim 15, wherein the tumor is a skin tumor and said medicament is formulated for intratumoral or topical or systemic administration.

20. A method according to claim 15, wherein said tumor is basal cell carcinoma or trichoepithelioma or a melanocytic tumor.

21. A method according to claim 20, wherein said medicament is a formulation comprising cyclopamine or a pharmaceutically applicable salt thereof and is topically applied onto the tumor about four times or more per day to deliver about 3.6 micromole or more of cyclopamine per day to each square centimeter of the surface area of the tumor on skin.

22. A method according to claim 21, wherein said medicament is in the form of a cream of cyclopamine.

23. A method for causing decrease of size or disappearance of a tumor in a human, comprising determining that Hedgehog/Smoothened signaling is utilized for inhibition of apoptosis of the tumor cells and administering to him or to her a medicament comprising cyclopamine or a pharmaceutically acceptable salt thereof or another selective inhibitor of Hedgehog/Smoothened signaling to induce apoptosis of the tumor cells to cause decrease of size or disappearance of the tumor.

* * * * *